(12) United States Patent
Grosskopf et al.

(10) Patent No.: US 9,672,625 B2
(45) Date of Patent: Jun. 6, 2017

(54) METHOD AND APPARATUS TO AUTOMATICALLY IMPLEMENT A SELECTION PROCEDURE ON IMAGE DATA TO GENERATE A SELECTED IMAGE DATA SET

(71) Applicant: Siemens Aktiengesellschaft, Munich (DE)

(72) Inventors: Stefan Grosskopf, Nuremberg (DE); Jing Lu, Shanghai (CN); Daniel Ruzicka, Nuremberg (DE); Michael Scheuering, Nuremberg (DE)

(73) Assignee: Siemens Aktiengesellschaft, Munich (DE)

( * ) Notice: Subject to any disclaimer, the term of this patent is extended or adjusted under 35 U.S.C. 154(b) by 213 days.

(21) Appl. No.: 14/294,241

(22) Filed: Jun. 3, 2014

(65) Prior Publication Data

US 2014/0355857 A1 Dec. 4, 2014

(30) Foreign Application Priority Data

Jun. 3, 2013 (DE) .......................... 10 2013 210 252

(51) Int. Cl.
*G06F 19/00* (2011.01)
*G06T 7/00* (2006.01)

(52) U.S. Cl.
CPC .......... *G06T 7/0022* (2013.01); *G06F 19/321* (2013.01); *G06T 2207/10072* (2013.01); *G06T 2207/30004* (2013.01)

(58) Field of Classification Search
None
See application file for complete search history.

(56) References Cited

U.S. PATENT DOCUMENTS

| 8,917,923 B2 | 12/2014 | Grosskopf et al. |
| 2004/0218796 A1* | 11/2004 | Ryner ................ G06T 19/00 382/131 |

(Continued)

FOREIGN PATENT DOCUMENTS

| CN | 101013503 A | 8/2007 |
| CN | 102542543 A | 7/2012 |
| WO | WO 2010097534 A1 * | 9/2010 ........... G06T 7/0081 |

OTHER PUBLICATIONS

WO 2010097534 A1, Sep. 2010.*

(Continued)

*Primary Examiner* — Matthew Bella
*Assistant Examiner* — Soo Shin
(74) *Attorney, Agent, or Firm* — Schiff Hardin LLP

(57) ABSTRACT

In a method and apparatus to automatically generate a selected image data set from an entirety of medical measurement data of an examination subject, the entirety of the measurement data of the examination subject is received as input data, and at least a portion of the measurement data is automatically analyzed with regard to a number of specific, topologically representative content feature parameter values of the examination subject selected measurement data from the entirety is made, with the selected data associated with defined, specific, topologically representative content feature parameter values. The selected measurement data are assembled into a selected image data set, as output data.

15 Claims, 7 Drawing Sheets

(56) References Cited

U.S. PATENT DOCUMENTS

| | | | | |
|---|---|---|---|---|
| 2006/0095429 A1* | 5/2006 | Abhyankar | ......... | G06F 19/3418 |
| 2008/0260221 A1* | 10/2008 | Unal | ...................... | G06K 9/342 |
| | | | | 382/128 |
| 2008/0292152 A1* | 11/2008 | Nekrich | ................. | G06Q 10/00 |
| | | | | 382/128 |
| 2012/0187300 A1* | 7/2012 | Gagnon | ................ | G01T 1/2985 |
| | | | | 250/362 |

OTHER PUBLICATIONS

WO 2010097534 A1, Machine Translation.*
Bi et al. "Automatic Descending Aorta Segmentation in Whole-Body PET-CT Studies for PERCIST-based Thresholding," IEEE, 2012 International Conference on Digital Image Computing Techniques and Applications (DICTA), Dec. 3-5, 2012, pp. 1-6.*
Guan et al., "Automatic Hot Spot Detection and Segmentation in Whole Body FDG-PET Images", Image Processing, 2006 IEEE International Conferenceon, IEEE 2006; pp. 85-88; (2006).
Ptak et al., "Radiation Dose is Reduced with a Single-Pass Whole-Body Multi-Detector Row CT Trauma Protocol Compared with a Conventional Segmented Method: Initial Experience", Radiology; vol. 229, No. 3; pp. 902-905; (2003).
Bi et al., "Automatic Descending Aorta Segmentation in Whole-Body PET-CT Studies for PERCIST-based Thresholding", Digital Image Computing Techniques and Applications (DICTA), International Conference; pp. 1-6; (2012).

* cited by examiner

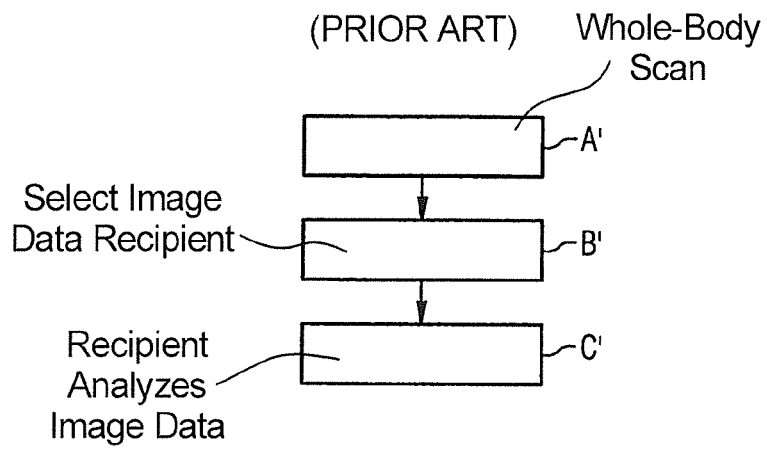
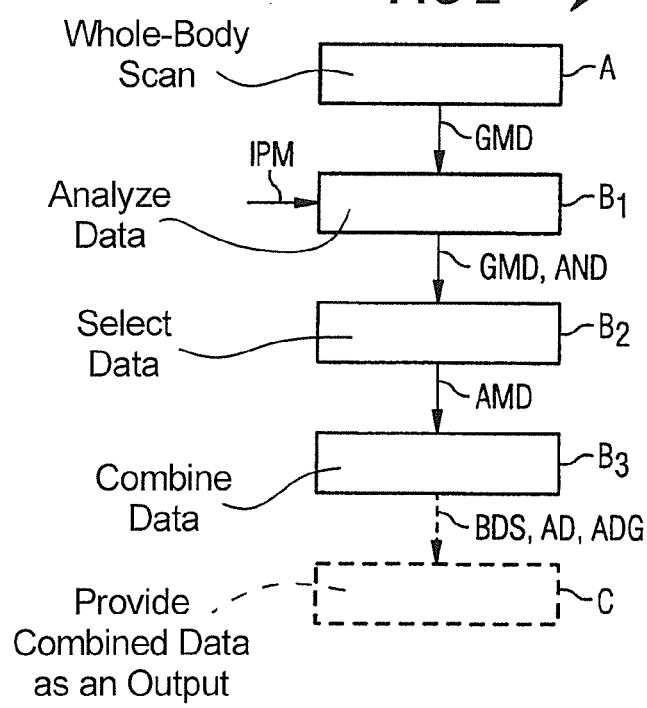

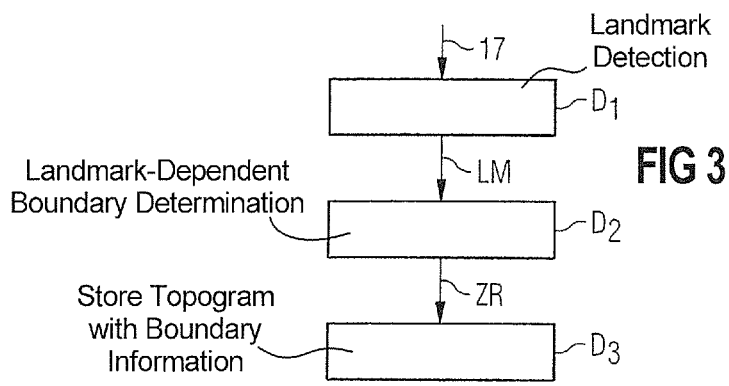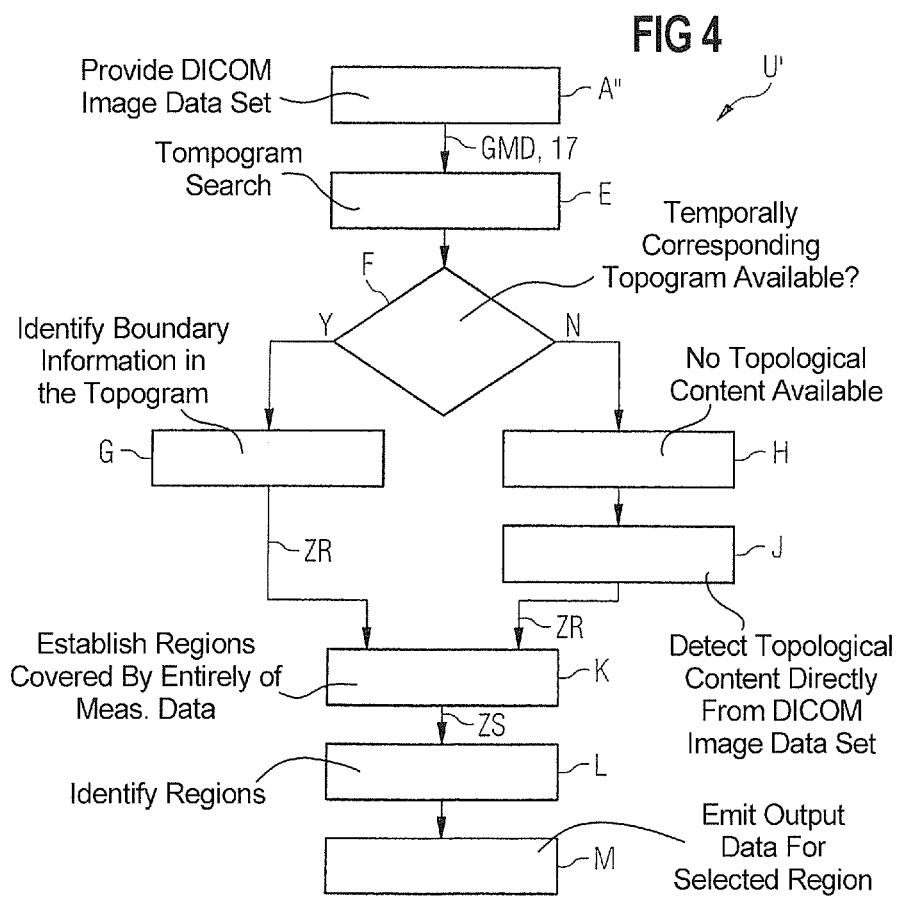

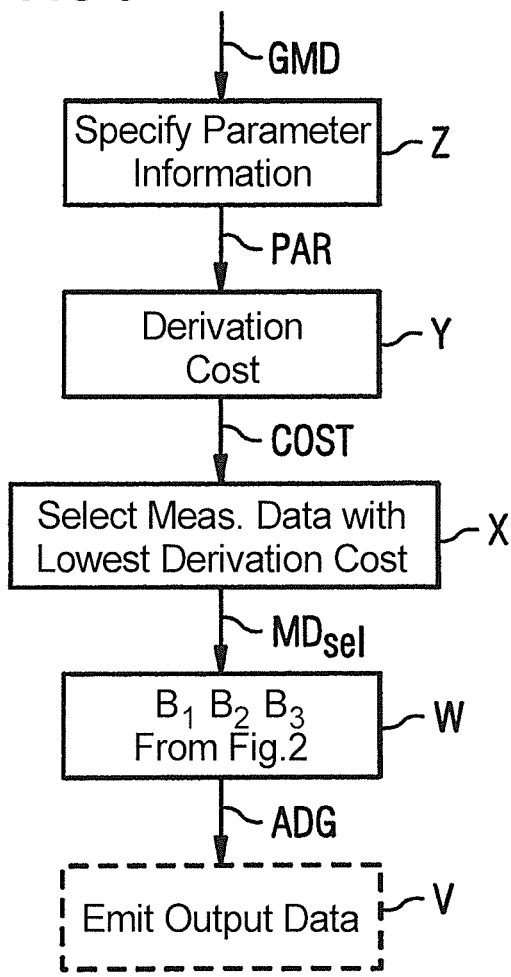

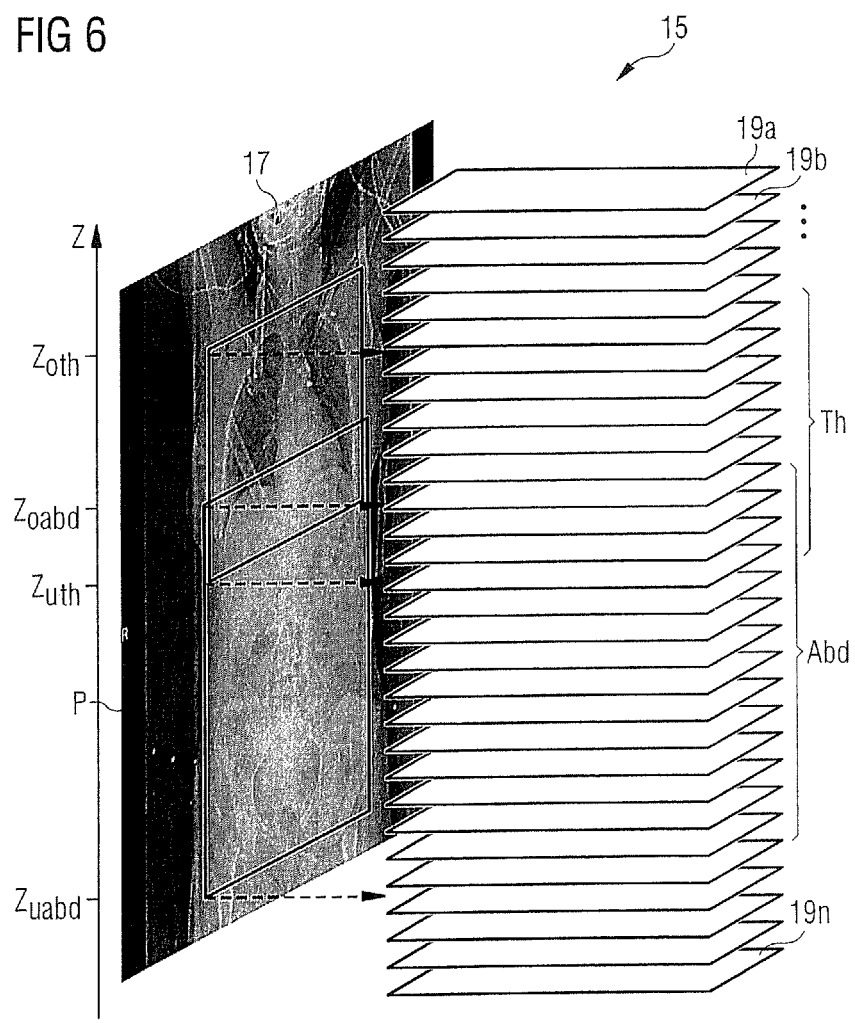

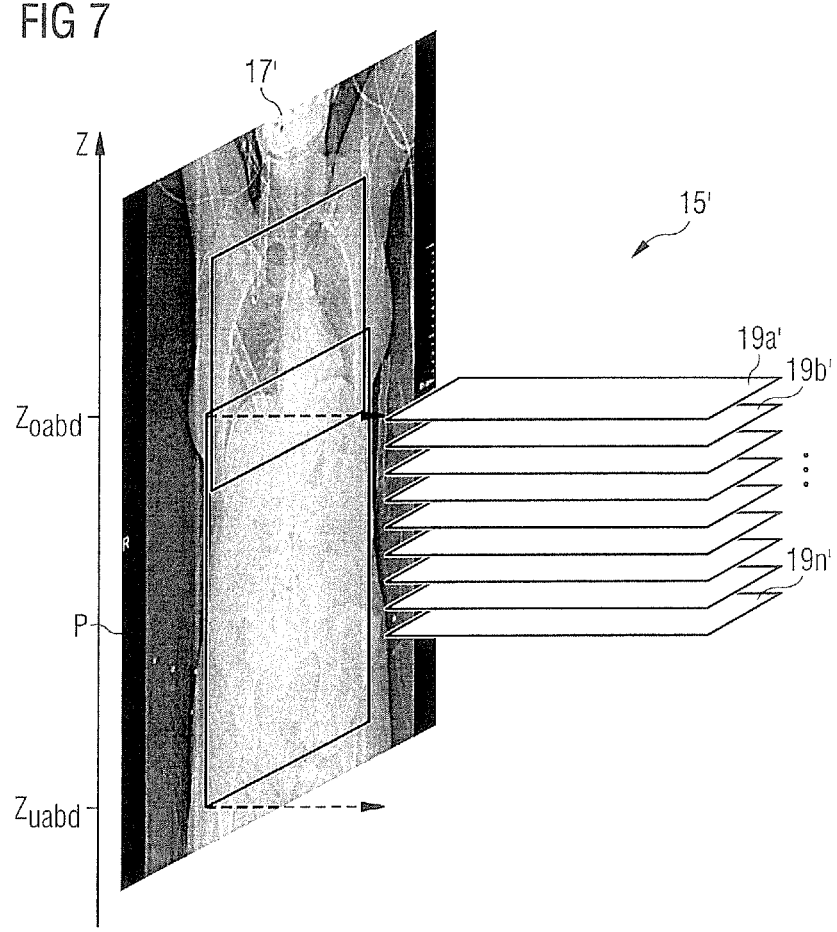

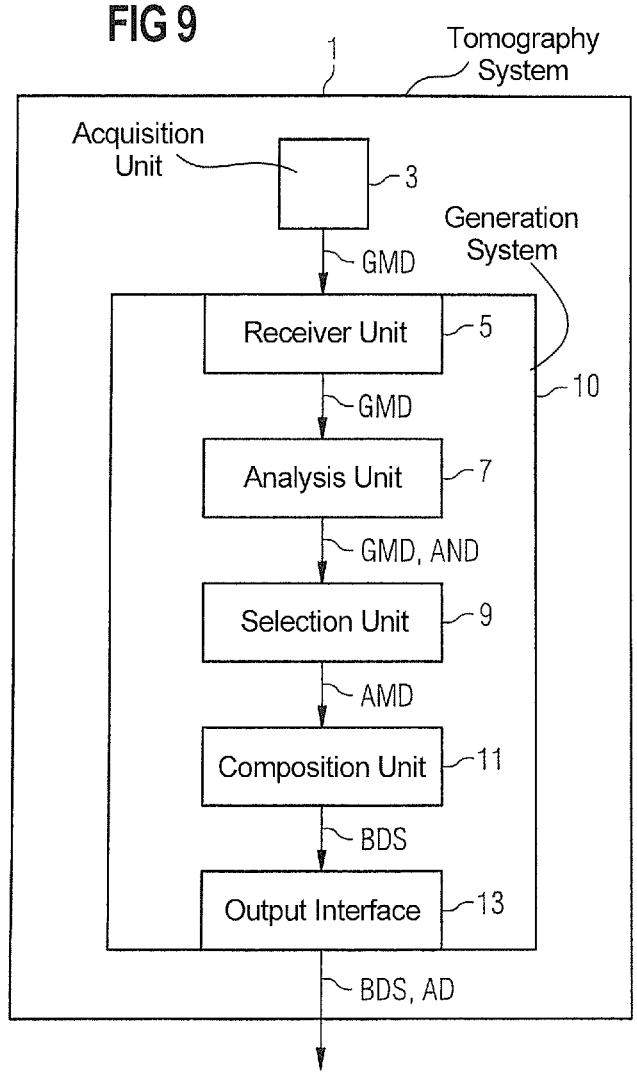

METHOD AND APPARATUS TO AUTOMATICALLY IMPLEMENT A SELECTION PROCEDURE ON IMAGE DATA TO GENERATE A SELECTED IMAGE DATA SET

BACKGROUND OF THE INVENTION

Field of the Invention

The present concerns a method to automatically generate a selected image data set from the entirety of a medical measurement data of an examination subject. Moreover, the invention concerns a system to automatically generate a selected image data set from the entirety of a medical measurement data of an examination subject.

Description of the Prior Art

For specific medical questions, regionally limited partial regions of an examination subject (such as a human body) are typically acquired with the use of imaging systems. For this purpose, the technician who conducts such a scan defines reconstruction parameters in advance before implementation of the scan by selecting a suitable scan protocol, and/or afterwards, depending on patient-specific requirements or in the interest of locating an abnormality.

However, in some cases it is necessary to scan larger partial regions of the patient or even his entire body in one pass in order to cover different areas of the body (or body regions; the two terms are used herein synonymously). For example, this is the case for body scans for comprehensive cancer diagnosis (for instance to detect metastases) or for polytrauma patients (for example patients after severe accidents). Different body regions (which are often also situated far from one another) of the body are thus scanned. Such body regions are (for example) the head, neck, thoracic and abdominal regions. These body regions are therefore situated one after another along the z-axis of a tomography system, i.e. along the direction in which the examination subject on a patient bed is introduced into the tomography system. In other words, they have a different coverage in the z-direction (thus a different z-coverage), and they may overlap somewhat in the z-direction. The measurement data (in particular the already reconstructed image data) from such larger-area scans can then be relayed in its entirety to a diagnosis workstation, for example, where the data are used for findings by a radiologist or by a specialist physician. However, the further use of this complete series of measurement data for assessment of individual partial regions (for instance individual organs) of the body is then very complicated, because now the assessor has more image data than are needed, and must still make numerous modifications after the fact, for instance a navigation to the body region to be assessed (windowing) or even the loading of multiple different whole-body series with different reconstruction parameters.

Therefore, it is preferred to pass the reconstructed image data separately (according to body regions) to a specialist who is concerned only with an individual data set. For this purpose, it is currently necessary for a technician or radiologist to subdivide the overall image data according to body regions in the form of sets known as DICOM data series, before he or she relays the data to the respective specialist. For this purpose, for each of the DICOM data series, the technician must define reconstruction parameters such as the respective windowing, the kernel (i.e. the convolution kernel in the reconstruction) and the slice interval of individual slice images of the image data from one another.

This process is time-consuming and laborious, and therefore is poorly suited to the clinical environment, in which tomography systems should be utilized as efficiently as possible, and in which the treatment speed (especially in the case of polytrauma patients) is decisive to being able to save a life or specific, endangered bodily functions.

SUMMARY OF THE INVENTION

An object of the invention is to simplify this selection process according to body regions, even independently of the type of reconstruction of the measurement data.

The invention provides for selected image data sets to be generated automatically and as effectively as possible. Moreover, preference is given to providing selected image data sets with optimally good resolution quality for the respective finding purpose.

A method according to the invention includes at least the following steps:

a) receive the entirety of the measurement data of the examination subject as input data. Such a receipt can also take place as a simple acceptance of the entirety of the measurement data (for example via an input interface of a processor-based system), and therefore can also be understood as an input of the entirety of the measurement data.

b) Analysis of at least a part of the measurement data with regard to a number of specific topologically representative content feature parameter values of the examination subject. For analysis, the entirety of the measurement data does not necessarily need to be (but can be) analyzed; rather, it can also suffice to analyze only a portion of the measurement data. The specific topologically representative content feature parameter values are to be understood as "specific" insofar as they are defined in advance and, for example, can in the further sense be selected depending on an intellectual interest of the later finding. Such an intellectual interest can relate both to the targeted detection of a defined illness or abnormality or injury within the examination subject and to the imaging of a selected partial region (for instance an organ or a defined structure) of the examination subject. In particular those content parameter values that concern a location or a spatially associable structure (for instance an organ or the like) are "topologically representative". Such a topologically representative parameter value can therefore include a location information, for instance a position in the examination subject in the z-direction (but also in the other spatial directions, for example, but also an association with a body organ (for instance the kidneys or the lungs).

c) Selection, from the entirety of such selected measurement data, of those that can be associated with defined, specific, topologically representative content feature parameter values. The selection of defined measurement data thus takes place on the basis of a selection of a number of specific, topologically representative content feature parameter values that in particular relate to a defined subject matter, for instance to a defined body region or (alternatively or additionally) to a defined body organ of the examination subject. The defined, specific, topologically representative content feature parameter values thus limit the measurement data to the effect that they are to be topologically associated with a space and/or a number of subjects within the body.

d) Assembly of the selected measurement data into a selected image data set as output data. Such a selected image data set can in particular preferably be assembled and stored as a contiguous DICOM data set.

Optionally (but preferably), in a step e) an output of the output data can subsequently take place. This output can be associated in a targeted manner with a specialist dealing with a defined body region of the examination subject, for instance output data regarding the head region and the spinal column with a neuro-radiologist or neurologist.

As used herein, "medical measurement data" are all conceivable measurement data from a medical acquisition system, in particular from a tomography system. For example, computed tomography (CT) systems, magnetic resonance (MR) systems, angiography systems, ultrasound apparatuses, x-ray apparatuses and positron emission tomography (PET) systems and single proton emission computer tomography (SPECT) systems are among such tomography systems. The acquisition data that are related to these systems are thus measurement data, which, as used herein, encompass both the raw data and reconstructed image data. Moreover, measurement data also include items known as topograms, thus image data from an overview scan of the respective examination subject.

As used herein, the "entirety" of the measurement data is not necessarily the entirety of all available measurement data of the examination subject, but rather that entirety that is fed in (i.e. is received in step a) within the scope of the method. This entirety can also (but does not need to) include measurement data from multiple different scans of the examination subject, for instance both a topogram from an earlier scan and reconstructed slice images from the earlier scan and from a current scan. Since such measurement data are normally stored in the DICOM format, in which the acquisition data and additional information are incorporated, they can also be temporally associated again at any time, but can also be mixed with one another in a targeted manner.

As used herein, an inanimate or animate body of an animal (i.e. also a human) organism can be an "examination subject". Therefore, in the following the term "examination subject" is synonymous with "patient".

An association of specific measurement data with a body region or, respectively, an organ region is thus implemented automatically with the aid of the method according to the invention. This takes place purely on the basis of the input measurement data, such that in the end an image-based recognition of the topologically representative content feature parameter values is implemented for which no additional user input is necessary. A user can then navigate in the output data. The user can even change from one selected image data set to another and thus inspect different body regions separately from one another. Respective, different views that are different for the respective body region (for example multiplanar reconstructions, MPRs; volume graphics, VRTs; maximum intensity projections, MIPs and many more), or output parameters (for instance windowing greyscales or volume graphic presets) can thereby be used.

According to the invention, a generation system of the aforementioned type includes at least the following components:

a) A receiver unit, for example fashioned as an input interface to receive the entirety of the measurement data of the examination subject as input data. The receiver unit can also include multiple receiver sub-units, for example a first input interface to receive topogram image data and a second input interface to receive reconstructed slice image data or the like.

b) An analysis unit that, in operation, analyzes at least a portion of the measurement data with regard to a number of specific topologically representative content feature parameter values of the examination subject.

c) A selection unit that, in operation, selects those selected measurement data that can be associated with defined, specific, topologically representative content feature parameter values.

d) A composition unit to assemble the selected measurement data into a selected image data set as output data.

e) Optionally, an output interface to show the output data in a humanly perceptible form.

Moreover, the invention concerns a tomography system with an acquisition unit and a generation system according to the invention. This means that the generation system according to the invention can be fashioned as part of the tomography system, for instance as part of an imaging processing system of the tomography system. The generation system can be realized therein as a separate unit but can also be integrated into arbitrary image processing devices.

The mentioned interfaces do not necessarily need to be designed as hardware components; rather, they can also be realized as software modules, for example if the measurement data can be received from another component (for example an image reconstruction device or other image processing unit or the like) already realized at the same apparatus must be passed only in software to another component. The interfaces can likewise be hardware and software components, for example a standard hardware interface that is specially configured for the concrete use case via software. Moreover, multiple interfaces can also be combined into a common interface, for example an input/output interface.

Overall, a majority of the components for realization of the generation system in the manner according to the invention (in particular the analysis unit, the selection unit and the composition unit) can be realized wholly or in part in the form of software modules on a processor.

The present invention also encompasses a non-transitory, computer-readable data storage medium encoded with programming instructions that, when the storage medium is loaded into a computerized processor, cause the processor to execute all steps of the method according to the invention as described above.

The entirety of the medical measurement data preferably includes reconstructed image data sets. This means that the raw data from the preceding scan before the implementation of the method according to the invention have already been reconstructed. It is thereby already possible to analyze within the reconstructed image data sets, and not to first implement a significantly more complicated analysis in the raw data that would need to follow a different and more complicated logic. Work in the reconstructed image data sets can thus take place with standard image analysis logic. Alternatively, raw data can first be reconstructed in the course of the method and then an analysis can take place downstream. The reconstructed image data sets preferably include a number of slices images. Selected slice images from these can then be assembled into the output data in the further course of the method.

It is additionally preferred that the entirety of the measurement data include a topogram of the examination subject, i.e. also of parts of the examination subject. This topogram is then particularly preferably analyzed in step b). The topographical analysis of the measurement data thus includes the analysis of a topogram from which the relevant topologically representative content feature parameter values can be particularly simply and efficiently extracted and used for subsequent selection. Instead of a pure analysis of the topogram, as an alternative or additionally the measurement data can also be analyzed, in particular as aforementioned reconstructed image data in step b). In this case, those measurement data that are considered later for a potential assembly into the output data would thus also be subjected to an analysis beforehand.

It has proven to be advantageous (because it is very effective) to use those topologically representative content feature parameter values in the analysis that include at least one landmark. For example, such landmarks can include a position of the examination subject in the z-direction or limitations of specific organs or, respectively, structures within the examination subject. Locations and positions within the examination subject can be concluded simply and quickly using these landmarks, wherein overall the topological analysis can be effectively optimized.

Furthermore, it is preferred that the topologically representative content feature parameter values—in particular a landmark of the topologically representative content feature parameter values—include anatomical features of the examination subject. In this context, all of the features that allow conclusions of the type or shape or, respectively, shape deviation or, respectively, volume or extent of an organ and/or a structure (for instance a bone structure or the like) of the examination subject are designated as anatomical features. These anatomical features can in particular also relate to the appearance or, respectively, the entirety of the examination subject, for instance in order to make a differentiation between the neck area and head area of a patient, for example purely based on the extent of the body of the patient in the transversal direction relative to the z-direction. Numerous other examples and differentiation possibilities are naturally also conceivable.

The topologically representative content feature parameter values can moreover include a boundary region information regarding the delimitation of an examination subject region (thus a region of the body), for example to delimit body regions among one another. However, it is also to be noted that body regions (for instance thorax and abdomen) in a person can necessarily also overlap, if only for the sake of certainty in order to ensure a guaranteed complete image coverage of a body region that transition regions of the body are then respectively associated with two body regions.

The method according to the invention can additionally be developed in that an extent of at least one body region of the examination subject is determined automatically in the measurement data and is used as a specific, topologically representative content feature parameter value in step c). It is thereby not the mathematical size of an extent of a subject that is designated as an extent but rather the length of the respective body region. It is thus initially determined what body regions extend from where to where, and then a selection of the measurement data is implemented via association of the measurement data with the respective body regions. This procedure can be implemented particularly simply, but nevertheless more unerringly and precisely, such that it quickly leads to very good results.

While the topologically representative content feature parameter values have previously been mentioned as a single analysis viewpoint, the method according to the invention can additionally incorporate further considerations and thereby be markedly refined. In this case, the output data are additionally assembled as multiple output data groups that can be differentiated from one another, according to additional auxiliary content feature parameter values that can be associated with defined measurement data of the output data. An additional selection within the output data thus takes place that leads to the situation that only defined output data that are to be associated with the auxiliary content feature parameter values are assembled into defined output data groups. For example, measurement data that are to be associated with a defined body region can thereby be understood as output data, and then defined image quality indicator values can be used as auxiliary content feature parameter values so that, from the output data, multiple groups of measurement data of one and the same body region with different image qualities can be assembled into the output data groups. For example, for a defined body region a first output data group (which could be subsumed under "soft part" images due to the underlying auxiliary content feature parameter values) can be generated from output data while a second output data group would be associated with "bone" images due to its underlying auxiliary content feature parameter values. In this context, an overview display can then be displayed to a user, in which a significant image and/or a data collection is provided per output data group, for example, so that the user can, on the basis of this, select (for example by clicking on a symbol) the output data group that is best suited to him.

It is additionally preferred that the auxiliary content feature parameter values include at least one of the following parameters:

a kernel, i.e. the convolution kernel of reconstructed image data that is used for a reconstruction, which kernel affects the sharpness or, respectively, resolution of these images, a slice thickness and/or a slice interval of slice images of the reconstructed image data, a search pattern, a field of view, meaning a number of parameter values that define or, respectively, characterize the x-coverage and/or y-coverage of the examination subject in the image acquisition, a z-coverage, meaning a coverage of the examination subject or, respectively, of a partial region of the examination subject in the feed direction in the image acquisition system, a spatial resolution (see further below in this regard), information regarding a modality that is used, thus regarding the tomography system that is used, a windowing information, i.e. a parameter value with regard to the windowing of the presentation values of the individual image points in the reconstructed image data, an information regarding a contrast agent injection and/or contrast agent phase: since contrast agent is often used in the imaging, especially given polytrauma patients, such parameter values relating to the contrast agent injection and/or contrast agent phase can be of particular relevance in this application case.

All of these parameters affect the image quality or, respectively, resolution of the reconstructed image data and are of different relevance in the finding depending on the intellectual interest, and are therefore to be selected (and possibly weighted) differently.

With regard to auxiliary content feature parameter values, it is especially preferred that these be input into a cost function with the goal of cost minimization and/or that the auxiliary content feature parameter values be prioritized according to a predetermined priority list. The auxiliary content feature parameter values are thus weighted among one another in a cost function, for example, and that output data group among multiple possible output data groups is selected that has the lowest cost according to the cost function. A selection of a defined output data group can analogously also take place using a priority list.

Within the scope of the method according to the invention (in particular given the development just described with formation of output data groups) it can occur that a body region is not entirely covered by the output data or, respectively, output data groups. Two developments of the invention that are based on this problem therefore exist in a) automatically determining a proportion of a coverage of a body region of the examination subject that is included in the output data and/or at least one output data group and/or b) automatically determining a proportion of a body region of the examination subject that is not included in the output data and/or at least one output data group.

An assessor is provided with information of what region coverage he achieves with his received output data or, respectively, with a defined output data group. The assessor can then possibly weigh whether he or she would rather select a different output data group with higher total coverage and lower resolution (or some other lower quality parameter values) instead of an output data group with lower total coverage and higher resolution (or some other higher quality parameter values), or vice versa. A tradeoff can thus be made here depending on the individual need for the relevant diagnosis or finding. This tradeoff can also be implemented automatically or semi-automatically within the scope of the method according to the invention, and in fact in particular in that that output data group (from multiple output data groups) is selected before output to a user that results (according to a pre-established weighting) in the ratio of coverage and compliance with requirements for quality parameter values that is best for the user. For this purpose, the user can enter inputs (for instance via a graphical user interface) for weighting that then lead to the output of the "optimal" output data group in an algorithm-based method on the basis of the present measurement data or output data.

Alternatively, an output algorithm can also be based purely on a body coverage, which means that that output data group with the lowest proportion of a body region of the examination subject that is not included in the output data group is automatically selected for output.

An additional use for the user in the assessment (or generally the further use of the output data or, respectively, output data groups) results if the output data and/or an output data group made up of the output data are identified with information regarding their underlying defined, specific, topologically representative content feature parameter values and/or additional auxiliary content feature parameter values. Associating or added an information (for instance in a DICOM header of a DICOM image data set that includes the output data or the output data group) that relates to the specific relevant feature parameter values with the output data or, respectively, an output group is thus an added value. This enables for the user a fast evaluation of the image data with regard to its coverage or, respectively, quality.

The method according to the invention is preferably applied within the scope of a whole-body scan since—as noted above—a division of the measurement data into individual regions must hereby take place particularly quickly and effectively. Therefore, the medical measurement data advantageously include those measurement data that result from a whole-body scan of the examination subject.

BRIEF DESCRIPTION OF THE DRAWINGS

FIG. 1 is a flowchart of a method according to the prior art.

FIG. 2 is a basic flowchart of a first exemplary embodiment of the method according to the invention.

FIG. 3 is a flowchart of an importation of a topogram within the scope of an exemplary embodiment of the method according to the invention.

FIG. 4 is a more detailed flowchart of a second exemplary embodiment of the method according to the invention.

FIG. 5 is a flowchart of a third exemplary embodiment of the method according to the invention.

FIG. 6 depicts a first topogram and a first number of slice images from which a selected image data set can be generated within the scope of the method according to the invention.

FIG. 7 depicts a second topogram and a second number of slice images from which a selected image data set can be generated within the scope of the method according to the invention.

FIG. 9 is a schematic block diagram of an embodiment of a tomography system according to the invention, with one embodiment of a generation system according to the invention.

DESCRIPTION OF THE PREFERRED EMBODIMENTS

Figure 8:
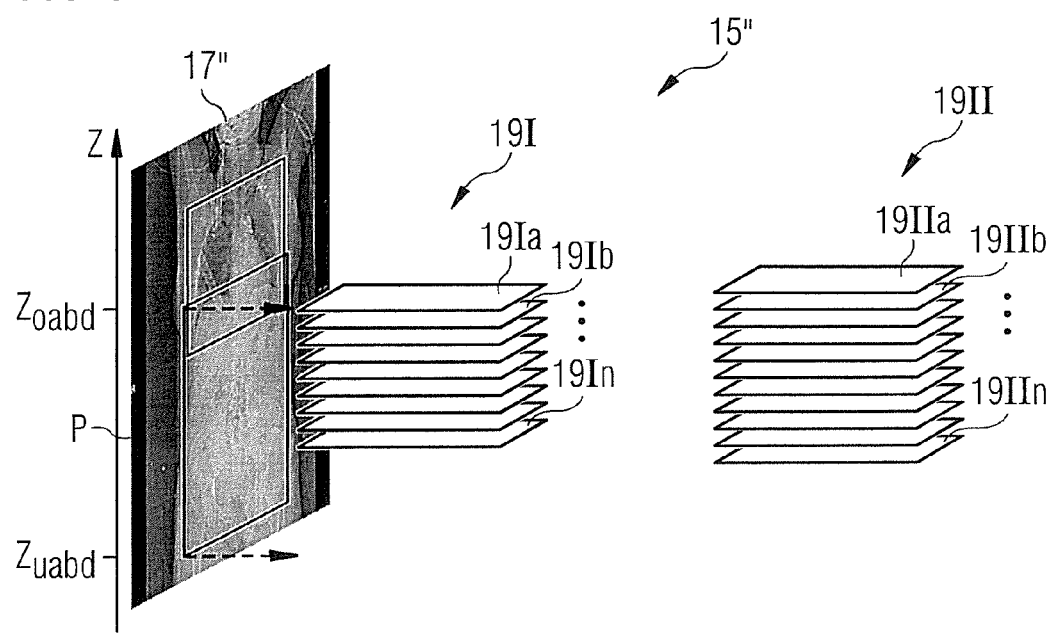
FIG. 8 depicts a third topogram and a third and fourth number of slice images from which a selected image data set can be generated within the scope of the method according to the invention.

FIG. 1 shows the basic workflow of a method according to the prior art. In a first step A', an examination subject (namely a human patient) is scanned. Since the present case deals with a whole-body scan, the patient is imaged from head to foot. A scan of the head therefore initially takes place, then the neck, then the torso, and then the lower extremities. The raw data are subsequently successively reconstructed from the scan, wherein each reconstruction of a body region can be implemented according to specific reconstruction parameter values defined in advance in a scan protocol. First all slice images of the head are thus successively reconstructed, then those of the neck, those of the thorax, those of the abdomen, of the pelvis and final those of the legs.

Now the purely user-controlled (manual) selection of image data according to body regions and their uploading to a workstation or, respectively, into the PACS of a clinic takes place in a second step B'. This step B' is thus not automatic but is based purely on user input, and accordingly on human judgment and experience. Step B' is accordingly demanding and time-consuming.

The selected image data are read in a third step C'. An additional user—normally a specialist for specific organs or, respectively, body regions—navigates through the data provided to him in step B' and serves therein for conspicuities to be assessed, for instance for injuries (for example a pneumothorax, a spinal column fracture, organ bleeding or the like) or, respectively, for pathological or conspicuous points such as tumors or the like.

In contrast to this, FIG. 2 shows the procedure according to an embodiment of the method U according to the present invention. Analogous to step A according to FIG. 1, an examination subject is again scanned in a step A. This scan process can be implemented in a step A' according to the prior art, wherein it is to be noted that it is also possible to implement the scan of the head and of the entire torso in one scan pass without interruption, whereby a faster scan is enabled but the resulting image quality also suffers somewhat in comparison to single region scans whose scan and reconstruction parameters can be predetermined in advance in a respective separate scan protocol. Measurement data result from the scan, for instance in the form of topogram measurement data from an overview scan and in the form of scan data, especially reconstructed image data. Within these measurement data, those measurement data are selected that are required for further processing in the method according to the invention, for instance because they offer a good overview for an analysis (see step $B_1$) and/or because they are themselves fundamentally considered for selection (see step $B_2$). All of these selected measurement data are designated as an entirety of measurement data (GMD) and are used further.

In the subsequent step $B_1$, an automatic analysis now takes place of at least a portion of this entirety GMD of the measurement data, from which analysis data AND result. The analysis $B_1$ thereby takes place based on (i.e. with regard to) specific, topologically representative content feature parameter values IPM.

In a step $B_2$, those selected measurement data AMD are then selected that can be associated with defined, specific, topologically representative content feature parameter values IPM, meaning that these include defined, specific, topologically representative content feature parameter values IPM or are compatible with these in terms of content or values.

In a step $B_3$, all selected measurement data AMD selected in the selection $B_2$ are combined into a selected image data set BDS so that output data AD or, respectively, (given a continuing selection according to other criteria, see in particular FIGS. 5 and 9) output data groups ADG result from this. These results can be output in an optional final step C, for example to a user for further processing and/or to a storage or archiving system (a PACS, for instance).

The method U is thus characterized in that the entirety GMD of the measurement data is automatically divided on the basis of topologically representative criteria, for example according to body regions of the examination subject. This division can be understood as a real separation of individual measurement data from one another into output data AD and other measurement data or, respectively, different output data groups ADG; however, it can also be understood as a simple selection and corresponding labeling of the selected measurement data. In particular, reconstructed image data that belong to the output data AD or, respectively, to an output data group ADG can thereby be displayed automatically, for example in a preferred position (i.e. perspective).

After step C, a user (for example a specialist physician) can then select a region or an organ or a structure of the examination subject (for instance by selecting an interface button) and then receives a presentation of exclusively the output data AD or, respectively, output data group(s) ADG that satisfy his selection criterion. The user can then again search therein for conspicuities to be assessed, for instance for injuries (for example a pneumothorax, a spinal column fracture, organ bleeding or the like) or for pathological or conspicuous points such as tumors or the like.

FIG. 3 shows the workflow of a topogram importation in order to use the topogram 17 in the following within the scope of an embodiment of the method according to the invention. The topogram 17 is thereby treated as belonging to the entirety GMD of the measurement data and examined in the analysis step $B_1$. The workflow shown here can therefore be viewed as one possible variant of an analysis $B_1$ within the scope of the method U according to the invention. The topogram 17 from the entirety GMD of the measurement data is subjected to a detection of landmarks LM comprised therein in a first step $D_1$. These landmarks LM can be regarded as topologically representative content feature parameter values IPM. In a second step $D_2$, based on the landmarks LM it is then determined in the topogram 17 where boundaries ZR of body regions and/or organs or, respectively, structures are located in said in the topogram 17, for example the upper and lower boundary of the thoracic region of a scanned patient. These two boundaries ZR define the z-coverage of the respective body region with regard to the z-direction of the tomography apparatus with whose aid the topogram scan was implemented.

In a third step $D_3$, the topogram 17 together with the boundary information ZR are stored in a database so that this information can be used for selection of the selected measurement data AMD in step $B_2$ of the method U according to the invention (see FIG. 2). In other words, the topogram 17 enhanced with the auxiliary information ZR can be used as a pre-marked orientation map for the following selection $B_2$.

FIG. 4 shows the principle workflow of a (refined) second exemplary embodiment of the method U' according to the invention. This method U' is based on the assumption that all available topograms 17 in the entirety GMD of measurement data that are dealt with here have already been evaluated in advance, for example with the aid of a method as it has been described using FIG. 3.

In a first Step A", reconstructed image data are provided in the form of what is known as a DICOM image data set (or multiple DICOM image data sets). These reconstructed image data can be enhanced by one (or more) topograms 17. Together with the topogram(s) 17, they represent the entirety GMD of the imported measurement data.

In a second step E, a query takes place as to whether a topogram 17 with regard to a defined scan is available, for instance in a database. For example, this can take place via a time query, i.e. via the query F as to whether a temporally corresponding topogram is present with regard to reconstructed image data that were acquired at a defined time. Given a positive response (Y), the workflow proceeds further with step G; given a negative response (N), the workflow proceeds with step H.

In step G, the boundary information ZR regarding defined body regions and/or organs or, respectively, structures is learned from the corresponding topogram 17.

In contrast to this, step H assumes that such information is not to be learned from a corresponding topogram 17. Therefore, here topologically representative content feature parameter values IPM (for example anatomical landmarks) are directly sought in the (three-dimensional) reconstructed image data of the appertaining DICOM image data set, from which the boundary information ZR regarding defined body regions and/or organs or, respectively, structures is learned again in the following step J.

In a step K that follows either step G or step J, it is established which regions of the body are covered by the entirety GMD of the measurement data. Boundary data ZS of the entirety GMD of the measurement data re thus determined. In step L, on the basis of the respective boundary information ZR regarding defined body regions or, respectively, organs or, respectively, structures and the upper and lower boundary ZS it is determined which parts of a body region or, respectively, of an organ or, respectively, structure are covered in the entirety GMD of the measurement data. It thereby applies that:

The boundary information ZR regarding a defined body region or, respectively, defined organ or, respectively, defined structure includes an upper boundary $z_{body\ region\ upper}$ and a lower boundary $z_{body\ region\ lower}$. The boundary data ZS of the entirety GMD of the measurement data include an upper boundary $z_{measurement\ data\ upper}$ and a lower boundary $z_{measurement\ data\ lower}$.

The z-coverage of the output data AD is calculated from the following relationship:

$$z\text{-coverage} = (\min(z_{body\ region\ upper}, z_{measurement\ data\ upper}) - \max(z_{body\ region\ lower}, z_{measurement\ data\ lower}))/(z_{measurement\ data\ upper} - z_{measurement\ data\ lower})$$

wherein "min" designates the smaller of the two above z-values and "max" designates the larger of the two above z-values.

In a step M, respective output data AD are then provided (for example stored) in the form of DICOM series, which output data AD are respectively additionally supplemented with information regarding the coverage determined in step L.

FIG. 5 shows a schematic workflow diagram of a third exemplary embodiment of the method according to the invention in which additional parameter values PAR are considered as auxiliary content feature parameter values PAR:

A specification of parameter values or, respectively, parameter information PAR regarding defined measurement data series within an entirety GMD of the measurement data takes place in a first step Z. These parameter values or parameter information PAR thus respectively relate to a measurement data series of a defined patient that form the basis of defined, identical presets in the image acquisition. For example, such presets or, respectively, the parameter values or parameter information PAR can relate to the scanned body region (for instance a thorax exposure), to the reconstruction kernel (for example the kernel B35f), to the slice interval of the individual slice exposures (for example 3 mm) or, respectively, to a search pattern (for example an angiographic search pattern).

In a second step Y, deviation cost COST are determined for each measurement data series of the entirety GMD of the measurement data. These deviation cost COST designate a deviation of sought optimum of a measurement data series, which optimum is defined in that (for example) precisely the desired parameter values or, respectively, parameter information PAR have been used in the image acquisition, and in that the z-coverage completely covers a defined body region or organ or structure that is to be examined.

The deviation cost COST can be determined with the aid of a cost function that is preferably formed according to the following scheme:

Deviation cost = $w_{z\text{-coverage}} \times (100\%\ z\text{-coverage})/100\%$ +

$w_{Slice\ interval} \times$ (Slice interval$_{Optimum}$ − Slice interval$_{Series}$)/1 mm +

$w_{Search\ pattern} \times 0$ or $1 + w_{kernel} \times dist$(kernal$_{Optimum}$, kernel$_{Series}$)

A weighting factor w is thereby associated with each influencing factor taken into account in the cost function (thus here the z-coverage, the slice interval, the search pattern and the kernel, wherein additional influencing factors can just as well be used), which weighting factor w is (for example) defined by the individual user, but can in principle also be established automatically.

The following costs are thus added up:

a) Cost for deviations from the complete z-coverage of the body region to be imaged: if this z-coverage is 100%, a factor of 0 automatically results.

b) Cost for deviations from optimal slice interval: costs generated per mm deviation of the slice interval of the measurement data series from the optimal (i.e. desired) slice interval, weighted with the weighting factor $w_{Slice\ interval}$. If the slice interval of the measurement data series corresponds to the optimal slice interval, a factor of 0 again results.

c) Cost for non-compliance with a desired search pattern: if the desired search pattern exists, a factor of 0 is set; otherwise a factor of 1.

d) Cost for differences of the kernel of the measurement data series from an optimal (i.e. desired) kernel: here a distance function dist is used that specifies the distance of the two kernels from one another, and that is multiplied with the weighting factor $w_{kernel}$.

This distance function dist can be composed as follows, for example: In the reconstruction of image data, the kernel is presently specified by four pieces of information that are explained using the kernel "B35f": the first letter (here "B") designates the characteristic of the kernel. The first figure (here "3") indicates the kernel sharpness, the second figure (here "5") designates the kernel version, and the second, lowercase letter at the end (here "f") designates the kernel mode.

The distance of a first kernel (here thus of the optimal kernel) from a second kernel (here thus of the kernel of the measurement data series) is calculated from the addition of four pieces of distance information that result from the aforementioned four pieces of information:

If the characteristic of the first kernel corresponds to that of the second kernel, "0" is set as a first distance information; otherwise, a predetermined characteristic constant $w_{Char}$ is set.

If the sharpness of the first kernel corresponds to that of the second kernel, "0" is set as a second distance information; otherwise, a predetermined sharpness constant $w_{Shar}$ is set.

If the version of the first kernel corresponds to that of the second kernel, "0" is set as a third distance information; otherwise, a predetermined version constant $w_{Vers}$ is set.

If the mode of the first kernel corresponds to that of the second kernel, "0" is set as a fourth distance information; otherwise, a predetermined mode constant $w_{Mod}$ is set. For example, 0.1 can be used as a value of the characteristic constant $w_{Char}$, the version constant $w_{Vers}$ and the mode constant $W_{Mod}$, and 1 can be used as a value of the sharpness constant $w_{Shar}$. This weighting of the individual constants relative to one another has yielded a very satisfactory result in the distance determination of kernels.

The cited distance information is added up, and the distance dist thus results that enters into the calculations that are explained further above.

In a third step X, that measurement data series $MD_{sel}$ that has the lowest deviation cost COST is selected on the basis of the respective deviation cost COST of the individual measurement data series. In a fourth step W, a selected image data set BDS including a body region (which selected image data set BDS forms an output data group ADG in the sense of the invention) is generated from this measurement data series $MD_{sel}$ on the basis of specific, topologically representative content feature parameter values IPM. The significant steps $B_1$, $B_2$, $B_3$ of the method Z according to the invention as they have already been described using FIG. 2 are thus combined in step W. The output data group ADG is then presented as output via a user interface in a fifth, optional step V.

FIGS. 6 through 8, which respectively show representations of topograms and a number of slice images, now serve to illustrate the exemplary embodiments.

FIG. 6 shows a first topogram 17 of a patient P, as well as additional measurement data that include a number of slices images 19a, 19b, . . . , 19n. Together, the topogram 17 and the slice images 19a, 19b, . . . , 19n form the entirety 15 of the measurement data 17, 19. Plotted at the edge of the topogram 17 is a z-axis that indicates the z-direction in which the patient P has been slid into a tomography apparatus in the image acquisition. The body of the patient P can be subdivided into a thorax region Th and an abdomen region Abd, just like the slice images 19a, 19b, . . . , 19n. This is easier to demonstrate using the topogram 17: the abdomen region Abd extends from a lower boundary $z_{uabd}$ of the abdomen Abd to an upper boundary $z_{oabd}$ of the abdomen Abd; the thorax region Th extends from a lower boundary $z_{uth}$ of the thorax Th to an upper boundary $z_{oth}$ of the thorax Th. The two regions Abd, Th thereby overlap somewhat so that the upper boundary $z_{oabd}$ of the abdomen Abd—as viewed from the lower boundary $z_{uabd}$ of the abdomen Abd—lies beyond the lower boundary $z_{uth}$ of the thorax Th. The boundaries $z_{uabd}$, $z_{oabd}$, $z_{uth}$, $z_{oth}$ have been determined using landmarks in the topogram 17. The respective slice images 19a, 19b, . . . , 19n that can be associated with one of the body regions thorax Th and abdomen Abd on the basis of the $z_{uabd}$, $z_{oabd}$, $z_{uth}$, $z_{oth}$ can be separated from one another with the aid of the method according to the invention, whereby the output data AD result as described above.

FIG. 7 shows second topogram 17' of a patient P with additional measurement data that include a number of slice images 19a', 19b', . . . , 19n'. The topogram 17' and the slice images 19a', 19b' . . . 19'n together form the entirety 15' of the measurement data. The additional measurement data 19' all lie completely within the region of the abdomen of the patient but do not cover the entire body region. If these additional measurement data 19' are therefore used as output data AD, only a partial z-coverage results.

FIG. 8 shows a third topogram 17" of a patient P with additional measurement data series 19I, 19II. The topogram 17" and the two measurement data series 19I, 19II together form the entirety 15" of the measurement data 17" 19I, 19II. The first measurement data series 19I includes a first number of slice images 19Ia, 19Ib, 19In; the second measurement data series 19II includes a second number of slice images 19IIa, 19IIb, . . . , 19IIn. Each of the two measurement data series 19I and 19II can be considered as an output data group ADG within the scope of the invention. As is apparent using the topogram 17", the first and second measurement data series 19I, 19II have different z-coverages. Which of these two measurement data series 19I, 19II or output data groups ADG is output to a user for further use can now be decided with the aid of a weighting method, as was explained using FIG. 5.

FIG. 9 shows a schematic block diagram of an embodiment of a tomography system 1 according to the invention, with an embodiment of a generation system 10 according to the invention and an acquisition unit 3.

The generation system 10 has a receiver unit 5 in the form of an input interface 5, an analysis unit 7, a selection unit 9, a composition unit 11 and an output interface 13.

The entirety GMD, 15, 15', 15" of the measurement data 17, 17', 17", 19, 19', 19I, 19II of a patient is received via the input interface 5. The analysis unit 7 analyzes at least a portion of the measurement data 17, 17', 17", 19, 19', 19I, 19II with regard to a number of specific topologically representative content feature parameter values IPM of the patient P and derives analysis data AND from these. The selection unit 9 selects selected measurement data AMD from the entirety GMD, 15, 15', 15" that can be associated with the wholly defined, specific, topologically representative content feature parameter values IPM, and the composition unit 11 assembles the selected measurement data AMD into a selected image data set BDS. This selected image data set BDS forms the output data AD that are output via the output interface 13.

Although modifications and changes may be suggested by those skilled in the art, it is the intention of the inventors to embody within the patent warranted hereon all changes and modifications as reasonably and properly come within the scope of their contribution to the art.

We claim as our invention:

1. A computerized method to automatically generate a selected image data set from an entirety of medical measurement data of an examination subject, comprising:
   providing a computerized processor with an entirety of measurement data representing a whole-body scan of an examination subject, as input data;
   in said processor, automatically analyzing at least a portion of said input data with respect to a plurality of topologically representative content feature parameter values of the examination subject and auxiliary content feature parameter values that have an effect, selected from the group consisting of image resolution and image quality, on image data to be reconstructed from said measurement data;
   in said processor, automatically selecting a subset of measurement data, from the entirety of said input data, comprised of measurement data that are associated with said topologically representative content feature parameter values and said auxiliary content feature parameter values;
   in said processor, automatically selecting a reconstruction algorithm dependent on the selected subset of measurement data, and using the selected reconstruction algorithm to reconstruct a selection image data set from said selected subset of measurement data, and formulating said selection image data set as output data; and
   in said processor, automatically selecting a recipient for said output data dependent on a content of said selection image data set, and making a designation of said selected recipient in electronic form from said processor.

2. The method as claimed in claim 1 wherein said entirety of said measurement data includes reconstructed image data sets that respectively include a plurality of slice images.

3. The method as claimed in claim 1 wherein the entirety of said measurement data includes a topogram of the examination subject, and wherein said portion of said measurement data that is analyzed includes said topogram.

4. The method as claimed in claim 1 comprising analyzing said at least a portion of said measurement data with regard to at least one landmark, as one of said topologically representative content feature parameter values.

5. The method as claimed in claim 4 wherein said at least one landmark is an anatomical landmark of the examination subject.

6. The method as claimed in claim 1 comprising analyzing said at least a portion of said entirety of said measurement data with respect to boundary region information that delimit an examination region of the examination subject, as said topologically representative contact feature parameter values.

7. The method as claimed in claim 1 comprising, in said processor, automatically determining an extent of at least one body region of the examination subject from said entirety of said measurement data, and using said extent of said at least one body region as a topologically representative content feature parameter value.

8. The method as claimed in claim 1 comprising selecting said auxiliary content feature parameter values from the group consisting of a convolution kernel, a slice thickness of slice images represented by said entirety of said measurement data, a slice interval of slice images represented by said entirety of said measurement data, a search pattern, a field of view representing coverage a medical instrument used to generate said entirety of measurement data, a coverage along a longitudinal axis of the examination subject by a medical device used to generate said entirety of said measurement data, a spatial resolution of said entirety of said measurement data, information identifying a modality used to generate said entirety of said measurement data, information identifying a contrast agent injection used to generate said entirety of said measurement data, information defining a contrast agent phase of contrast agent used to generate said entirety of said measurement data, and windowing information used in generating said entirety of said measurement data.

9. The method as claimed in claim 1 comprising entering content feature parameter values that are used to differentiate said plurality of output data groups, into said processor in a cost function that minimizes statistical costs associated with the respective content feature parameter values.

10. The method as claimed in claim 1 comprising, in said processor, prioritizing said content feature parameter values that are used to select said selected recipient, according to a predetermined priority list in said processor.

11. The method as claimed in claim 1 comprising, in said processor, automatically selecting a plurality of subsets of measurement data, from the entirety of said input data, each respectively comprised of measurement data that are associated with different topologically representative content feature parameter values and, for each subset, automatically determining a proportion of coverage of a body region represented by that respective subset, with respect to a body region of the examination subject represented by another of said subsets.

12. The method as claimed in claim 11 comprising identifying the subset for which said proportion is lowest, and selecting said selected recipient dependent on the measurement data in said subset for which said proportion is lowest.

13. A system to automatically generate a selected image data set from an entirety of medical measurement data of an examination subject, comprising:
a computerized processor having an input provided with an entirety of measurement data representing a whole-body scan of an examination subject, as input data;
said processor being configured to automatically analyze at least a portion of said input data with respect to a plurality of topologically representative content feature parameter values of the examination subject and auxiliary content feature parameter values that have an effect, selected from the group consisting of image resolution and image quality, on image data to be reconstructed from said measurement data;
said processor being configured to automatically select a subset of measurement data, from the entirety of said input data, comprised of measurement data that are associated with said topologically representative content feature parameter values and said auxiliary content feature parameter values;
said processor being configured to automatically select a reconstruction algorithm dependent on the subset of selected measurement data, and use the selected reconstruction algorithm to reconstruct a selection image data set from said selected subset of measurement data, and formulate said selection image data set as output data; and
said processor being configured to automatically select a recipient for said output data dependent on a content of said selection image data set, and to make a designation of said selected recipient in electronic form from said processor.

14. A tomography system comprising:
a topographic data acquisition scanner configured to execute a whole body scan of an examination subject to acquire an entirety of tomographic medical measurement data from the examination subject;
a computerized processor having an input provided with said entirety of said tomographic medical measurement data obtained from said examination subject, as input data;
said processor being configured to automatically analyze at least a portion of said input data with respect to a plurality of topologically representative content feature parameter values of the examination subject and auxiliary content feature parameter values that have an effect, selected from the group consisting of image resolution and image quality, on image data to be reconstructed from said measurement data;
said processor being configured to automatically select a subset of measurement data, from the entirety of said input data, comprised of measurement data that are associated with said topologically representative content feature parameter values and said auxiliary content feature parameter values;
said processor being configured to automatically select a reconstruction algorithm dependent on the selected subset of measurement data, and use the selected reconstruction algorithm to reconstruct a selection image data set from said selected subset of measurement data, and to formulate said selection image data set as output data; and
said processor, being configured to automatically select a recipient for said output data dependent on a content of said selection image data set, and to making a designation of said selected recipient in electronic form from said processor.

15. A non-transitory, computer-readable data storage medium encoded with programming instructions that, when said storage medium is loaded into a computerized processor, cause the processor to:
receive an entirety of measurement data representing a whole-body scan of an examination subject, as input data;
analyze at least a portion of said input data with respect to a plurality of topologically representative content feature parameter values of the examination subject and auxiliary content feature parameter values that have an effect, selected from the group consisting of image resolution and image quality, on image data to be reconstructed from said measurement data;

select a subset of measurement data, from the entirety of said input data, comprised of measurement data that are associated with said topologically representative content feature parameter values and said auxiliary content feature parameter values;

select a reconstruction algorithm dependent on the selected measurement data and use the selected reconstruction algorithm to reconstruct a selection image data set from said selected subset of measurement data, and formulate said selection image data set as output data; and automatically select a recipient for said output data dependent on a content of said selection image data set, and making a designation of said selected recipient in electronic form from said processor.

* * * * *